United States Patent [19]

Baumberg

[11] Patent Number: 4,807,988

[45] Date of Patent: Feb. 28, 1989

[54] METHOD AND DEVICE FOR EVALUATING VISION

[76] Inventor: Iosif Baumberg, 69 Bay 29 St., Brooklyn, N.Y. 11214

[21] Appl. No.: 946,720

[22] Filed: Dec. 29, 1986

[51] Int. Cl.[4] .............................................. A61B 3/14
[52] U.S. Cl. ..................................... 351/210; 351/200
[58] Field of Search ................ 351/210, 203, 239–245, 351/200, 202

[56] References Cited

U.S. PATENT DOCUMENTS 3,992,087  11/1976  Flom et al. .......................... 351/210
4,611,583   9/1986  Wasserman .......................... 351/203

Primary Examiner—Rodney B. Boverick
Assistant Examiner—P. M. Dzierzynski

[57] ABSTRACT

The present invention relates to a method and device for evaluating vision in humans. One feature of the present invention resides in a method and a device in which a plurality of symbols spaced from one another are moved and their speed of movement is adjusted so that the symbols become visible by a person to be evaluated as stationary symbols which appear in certain time intervals.

At this point, an average statistic frequency of symbol appearance corresponds to the frequency of jumps of the person's eyes in direction of the symbols movement, while the value of the speed of the symbols movement at which they appear as stationary corresponds to an approximate speed of the person's eyes during the jumps.

3 Claims, 1 Drawing Sheet

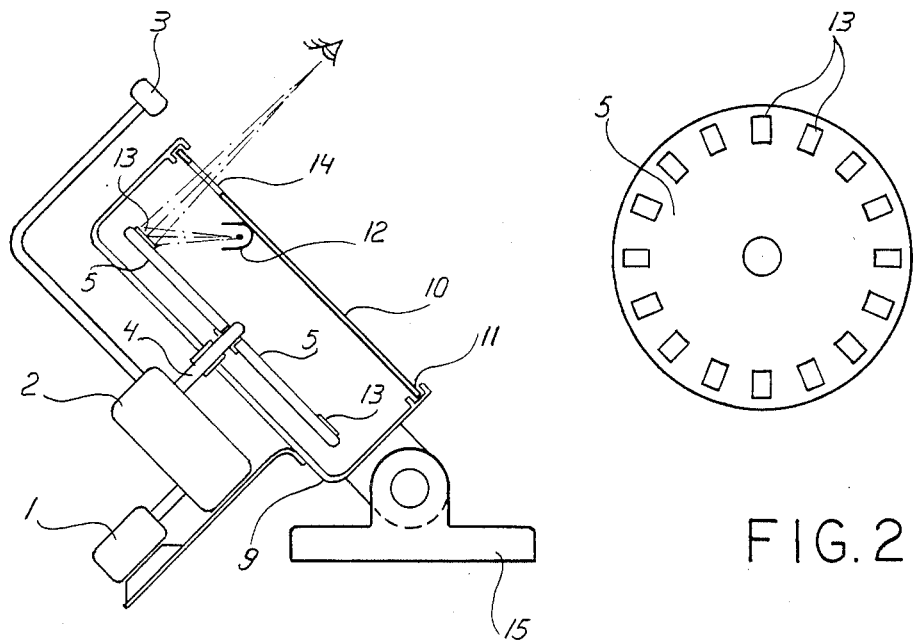
FIG. 2
FIG. 1
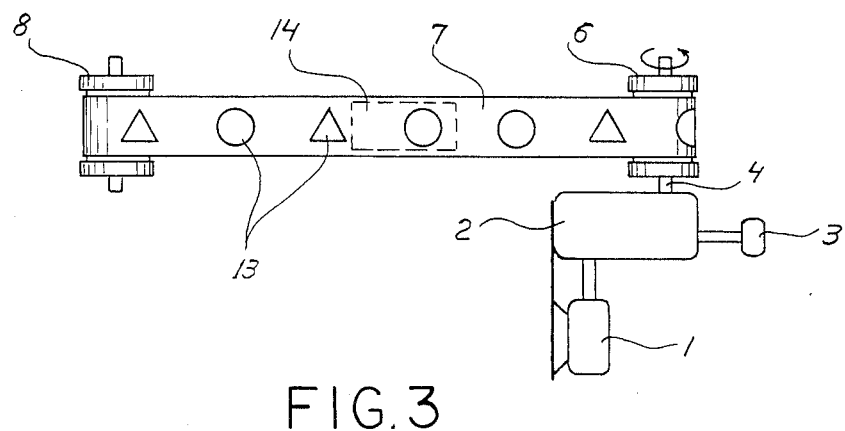
FIG. 3

METHOD AND DEVICE FOR EVALUATING VISION

BACKGROUND OF THE INVENTION

The present invention relates to a method of and a device for evaluation of vision.

It is known that a human eye and in particular retinae has an area of highest resolution and best color determination—its central cavity of fovea. The latter contains densely located receptors which are sensitive to color. Fovea which possesses highest information capability has the size of 2°. Smallness of this part is compensated by eye's ability to perform sharp jump-like movements by an angle up to 20°. Because of this images of areas of observation are successively projected into the fovea, and therefore the sharpness of vision is distributed over larger field that the area of fovea. In addition, objects which move with angular speeds which are close to the angular speed of eye movement during the jumps become recognizable despite the fact that at these angular speeds they are not only not recognizable, but even flickering of them cannot be seen.

Jump-like movements of eyes takes place at an average of 2–5 times per second. The values of time intervals between two successive eye jumps are distributed randomly, which precludes flickering of images. Frequency and speed of jump-like movements of eyes are different for different people and change with ago and health changes. Evaluation of jump-like movements of individuals is very important for evaluating their vision. Objective evaluation of frequency (average statistic frequency) and speed of jump-like movement of eyes is very important for determining whether given individuals are capable and can be permitted to do certain jobs which require a wide angle of vision, high shaprness of vision, and fast reaction. It can also be used for controlling health of patients in insurance systems.

It is known for purely scientific purposes to investigate jump-like eye movement by a light beam reflected from a mirror which is attached to the eye of a patient. This is a very complicated and dangerous procedure which cannot be use by ophtalmologists for regular eye examinations especially of great number of people. Moreover an eye with the attached mirror does not provide objective results since it acts in abnormal manner.

SUMMARY OF THE INVENTION

Accordingly, it is an object of the present invention to provide a method of and a device for evaluating vision, which is objective, simple and accurate, as pertaining to determination of parameters of jump-like movements of human eyes.

It is also an object of the present invention to provide a method of and a device for evaluation of vision in night time (less than $10^{-2}$lx) and day time (more than $10^2$lx).

In keeping with these objects and with others which will become apparent hereinafter, one feature of the present invention resides, briefly stated, in a method and a device in which a plurality of symbols spaced from one another are moved and their speed of movement is adjusted so that the symbols become visible by a person to be evaluated as stationary symbols which appear in certain time intervals.

At this point, an average statistic frequency of symbol appearance corresponds to the frequency of jumps of the person's eyes in direction of the symbols movement, while the value of speed of symbols movement at which they appear as stationary corresponds to an approximate speed of the person's eyes during the jumps.

In accordance with another embodiment of the invention, the symbols are different in shape (circles, triangles etc) and/or color etc., and their number is irregular.

The device can be provided with a light source with adjustable brightness, to provide evaluation corresponding to day time or night time vision.

The symbols carrier can be formed as a band which is rewindable or endless. It can be of one color while the symbols can be of another color.

The novel features of the present invention are set forth in particular in the appended claims. The invention itself, however, will be best understood from the following description of preferred embodiments which is accompanied by the following drawings.

BRIEF DESCRIPTION OF THE DRAWINGS

FIG. 1 is a view showing a device for evaluation of vision in accordance with the present invention;

FIG. 2 is a view shematically showing a carrier of the device of FIG. 1;

FIG. 3 is a view showing the inventive device in accordance with another embodiment of the invention.

DESCRIPTION OF PREFERRED EMBODIMENT

A device for evaluation of vision and more particularly for evaluation of jump-like movements of person's eyes includes a motor 1, for example a synchronous electric motor (FIG. 1) with an output shaft which is coaxially connected with an input shaft of reducer 2 with adjustable ratio. The adjustment of the ratio is performed from a control board by a handle 3. An output shaft 4 of the reducer supports a flat circular disc 5 with a plurality of symbols circumferentially spaced from one another by equal distances. The symbols are identified as 13 and can be formed by films. In the embodiment of FIG. 3 the output shaft is provided with a roller 6 which drives a band 7 with a plurality of symbols over itself and over a driven roller 8.

In the embodiment of FIG. 1 the symbols carrier 5 is located in a non-transparent casing 9 with a front flat wall 10 which can rotate in a groove 11. A light source 12 is located inside the casing and has two working modes—dark (twilight) illumination and day illumination. An observation window 14 is provided in the front wall. The height of the window 14 (radial in FIG. 2, transverse in FIG. 3) is selected so that the whole height of the symbols can be seen therethrough. The width of the window 14 in the direction of carrier movement (circumferential in FIG. 2, longitudinal in FIG. 3) is selected so that it is greater than the sum of a distance between two neighboring symbols and a width of one symbol in the same direction. The front wall 10 is turnable in the groove 11 and can be fixed in any angular position by known fixing means.

The device is supported in a base 15 and can be turned relative to the latter to by fixed at any angle, between a position in which the symbols are arranged and move in a horizontal plane and a position in which the symbols are arranged and move in a vertical plane.

The device can be provided with a set of carriers which have windows of different width, carriers for evaluation of night (twilight) vision and day vision, carriers with symbols of two or more shapes and colors of symbols.

The device in accordance with the present invention operates in the following manner. The casing 9 is set relative to the base at an angle which is convenient for a person to be examined. A respective carrier 5 or 7 are fitted onto the shaft 4. The light source 12 is adjusted to a desired mode, and the motor 1 is turned on. With the handle 3 the ratio of the reducer and therefore the speed of movement of the carrier is adjusted until the person sees the symbols and periodically appearing as stationary in the window, and any speed increase or decrease leads to a worse visibility of the symbols. The average statistic frequency of appearance of stationary symbols in the window characterizes an average statistic frequency of jumps of patient eyes, while the speed of carrier movement at which the above phenomenon takes place characterizes an average speed of movement of patient's eyes during the jumps.

For determining the above for day time or twilight (night) time, the light source is adjusted to provide the respective illumination intensity of the carrier and the symbols. For evaluation of eyes jumps from left to right, from up to down, from right to left, from down to up, the front wall is turned so that the window occupies relative to the carrier of FIG. 2 the positions corresponding to 12, 3, 6 and 9 o'clock respectively.

For preventing intentionally false statements by a person to be examined, the symbols are of different shape or color whose number is known only to a physician. The ratio between the symbols visible by a patient can be easily compared with the ratio known to the physician, to determine whether the patient tells the truth.

The invention is not limited to the details shown since various modifications and structural changes are possible without departing from the spirit of the present invention.

What is desired to be protected is set forth in particular in the appended claims.

I claim:

1. A method of evaluating vision, comprising the steps of providing a carrier with a plurality of symbols spaced from one another;

moving said carrier with said symbols in a predetermined direction while a person to be evaluated is observing the symbols;

adjusting a speed of the movement to such a speed at which the symbols moving with the carriers appear to a person to be evaluated during his observation of the symbols, as stationary periodically appearing symbols; and determining an average frequency of jump-like eye movements of the person during his observation of the symbols in correspondence with an average frequency of the appearance, and a speed of jump-like eye movements of the person during his observation of the symbols in correspondence with the adjusted speed.

2. A method as defined in claim 1; and further comprising the step of illuminating the symbols in at least two modes so as to evaluate the vision in at least two modes.

3. A method as defined in claim 1, wherein said providing step includes providing the carrier with one color and a plurality of symbols of another color.

* * * * *